United States Patent [19]

Harris

[11] 4,196,734
[45] Apr. 8, 1980

[54] COMBINED ELECTROSURGERY/CAUTERY SYSTEM AND METHOD

[75] Inventor: Frank W. Harris, Boulder, Colo.

[73] Assignee: Valleylab, Inc., Boulder, Colo.

[21] Appl. No.: 878,529

[22] Filed: Feb. 16, 1978

[51] Int. Cl.² .................. A61B 17/36; A61N 3/00
[52] U.S. Cl. ..................... 128/303.1; 128/303.14;
   128/303.15; 128/303.17; 219/233; 219/240; 219/241
[58] Field of Search ........... 128/303.1, 303.13–303.19; 219/233–235, 240, 241

[56] References Cited

U.S. PATENT DOCUMENTS

| 1,787,709 | 1/1931 | Wappler | 128/303.14 |
| 3,461,874 | 8/1969 | Martinez | 128/303.17 |
| 3,662,151 | 5/1972 | Haffey | 219/233 |
| 3,768,482 | 10/1973 | Shaw | 128/303.1 |
| 3,826,263 | 7/1974 | Cage et al. | 128/303.1 |
| 3,870,047 | 3/1975 | Gonser | 128/303.14 |
| 3,875,945 | 4/1975 | Friedman | 128/303.14 |
| 4,074,719 | 2/1978 | Semm | 128/303.1 |

FOREIGN PATENT DOCUMENTS

| 179607 | 2/1954 | Fed. Rep. of Germany | 128/303.17 |
| 166452 | 1/1965 | U.S.S.R. | 128/303.17 |

OTHER PUBLICATIONS

Sugita et al., "Bipolar Coagulator . . . ", J. Neurosurg., vol. 41, Dec. 1944, pp. 777–779.

*Primary Examiner*—Lee S. Cohen
*Attorney, Agent, or Firm*—Gerald J. Ferguson, Jr.; Joseph J. Baker

[57] ABSTRACT

A combined electrosurgery/cautery system wherein a common heater/electrode element is employed to effect electrosurgical and cautery procedures.

39 Claims, 11 Drawing Figures

FIG.3
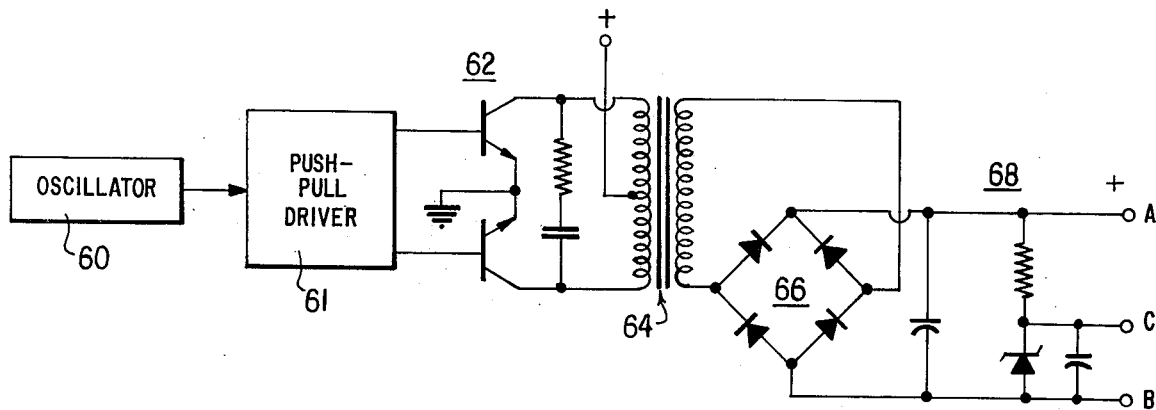
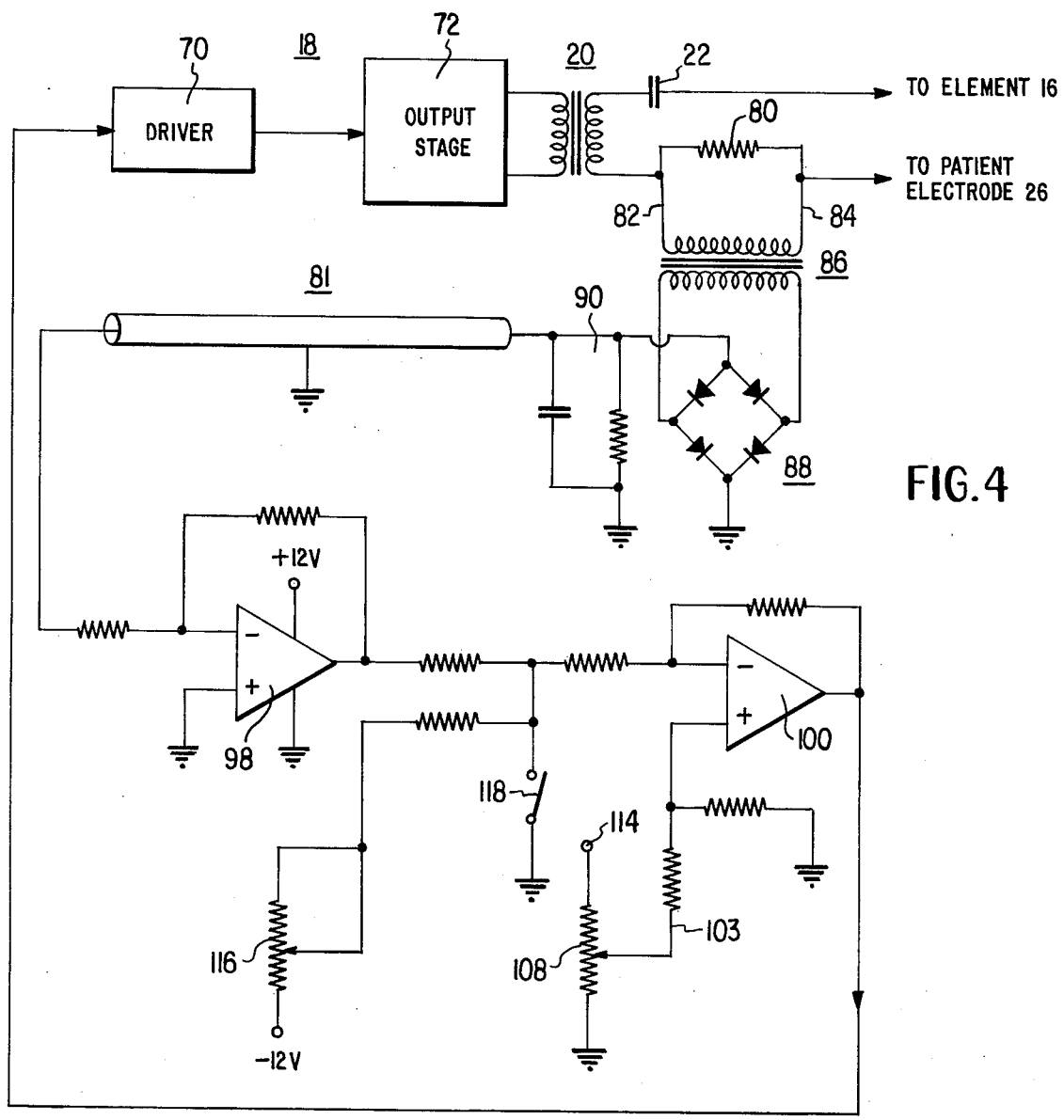
FIG.4

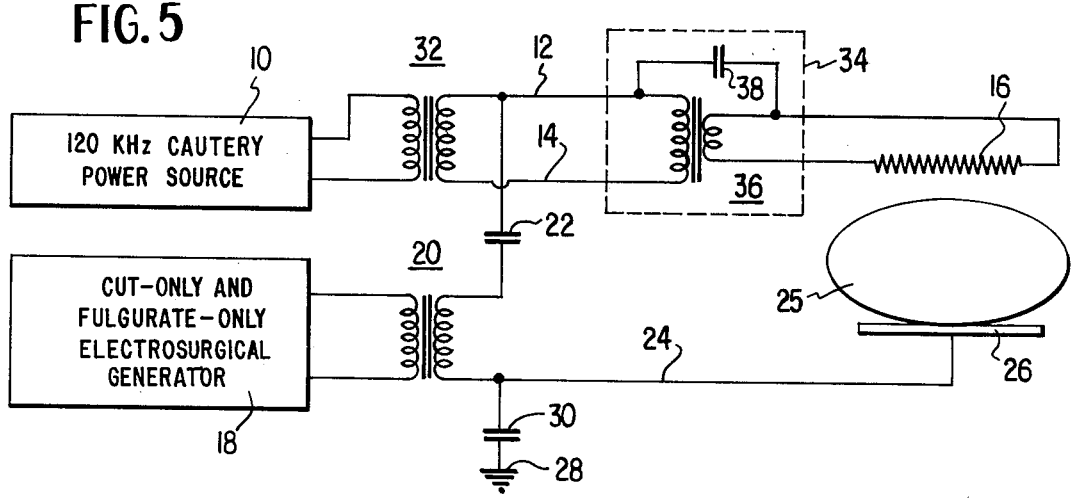
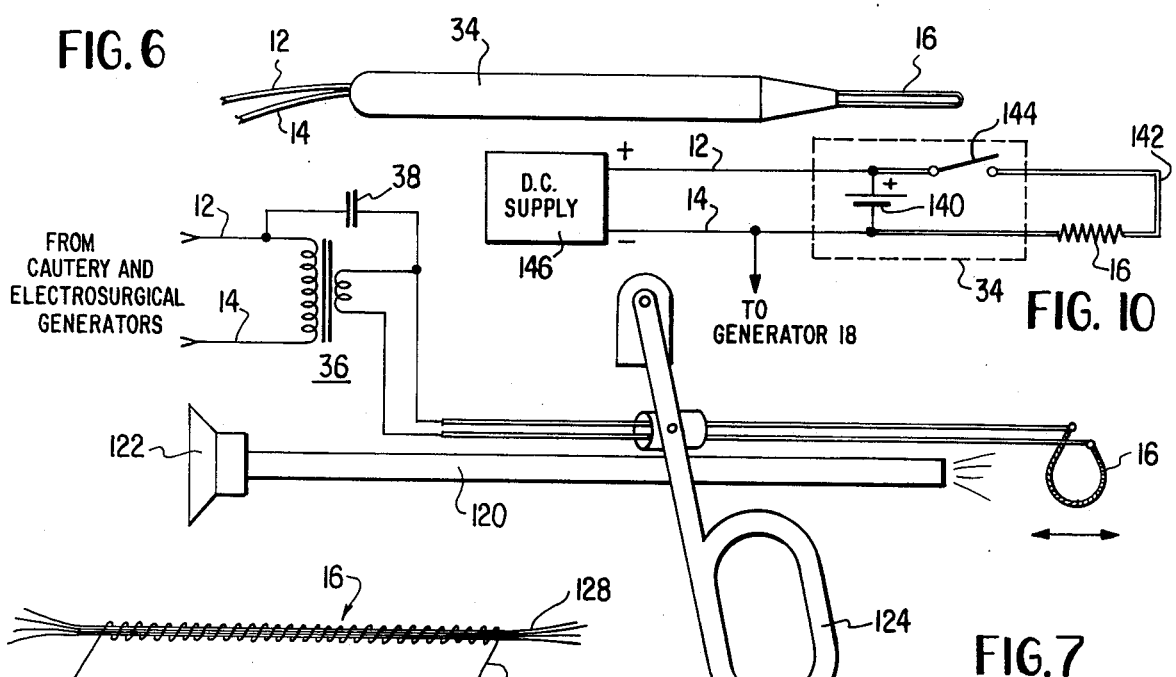
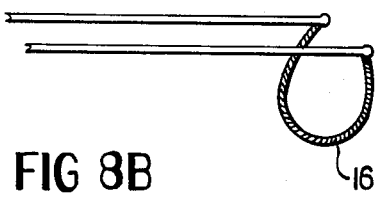
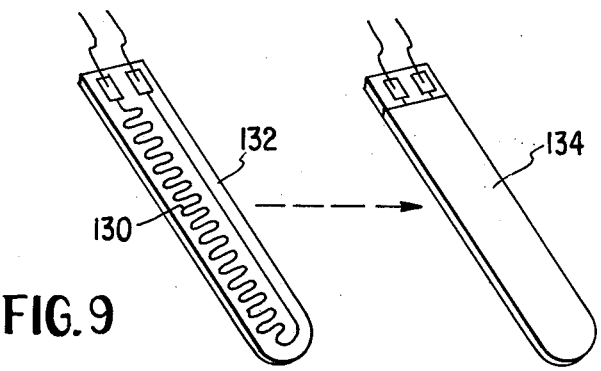

COMBINED ELECTROSURGERY/CAUTERY SYSTEM AND METHOD

CROSS-REFERENCE TO RELATED APPLICATIONS

This invention is related to (1) a U.S. application filed Jan. 12, 1978 by Frank W. Harris entitled "Improved Multiple Source Electrosurgical Generator" (hereinafter Application No. 1) and (2) U.S. Application Ser. No. 852,431 filed by Frank W. Harris on Nov. 17, 1977 and entitled "Contact Area Measurement Apparatus and Method for Use with Electrosurgery and Cryosurgery". Both of the foregoing applications are incorporated herein by reference.

BACKGROUND OF THE INVENTION

This invention relates to a unique electrosurgery/cautery system.

In the following specification and claims, a distinction is made between the terms electrosurgery and cautery. In electrosurgery, radio frequency current flows into the tissue being treated from a first electrode usually termed the active electrode. The current usually exits at a second electrode termed the patient or indifferent electrode although, as will be brought out in more detail hereinafter, the patient electrode does not necessarily have to be employed in accordance with one aspect of the present invention. Electrical interaction between the active electrode and tissue at the treated site may either be ohmic (to thereby effect a desiccation mode of operation) or by electrical arc (to thereby effect a cut or fulguration mode of operation). In cautery an element such as a wire is electrically heated by passing a current therethrough, the cautery element typically being used to seal bleeding blood vessels in hospital surgical procedures and in minor surgery performed in doctors' offices. Hence, in summary, an important distinction between electrosurgery and cautery is that in the former current flows through the patient's tissue while in the latter current is restricted to the heating element.

In electrosurgery there are three effects which may be produced by passing radio frequency current through tissue—namely, desiccation, cutting and fulguration. In desiccation, the active electrode is held in firm contact with the tissue with the current passing directly into the tissue and the heating effect being brought about by $I^2R$ heating. Thus, the mode of operation is ohmic.

In cutting, the active electrode is not in good contact with the tissue and electric sparks jump from the electrode to the tissue. The voltage waveform used is generally a sinewave and the sparks are short in length but heat the tissue intensely. The cells burst into steam and the steam maintains the layer of gas between the electrode and the tissue as the incision proceeds. In order to produce a cutting effect without desiccation, the generator must be current limited to less than about 200 milliamperes.

In fulguration, the coagulation occurs by means of a high voltage spark which jumps from the active electrode to the tissue. Thus, an arcing mode of operation occurs in both cuting and fulguration. The spark produces intense heating at every point it strikes, but a high crest factor voltage waveform, called a COAG waveform, makes long sparks and distributes the spark widely. This keeps the energy density down and minimizes the cutting effect.

Of the three electrosurgical modes, desiccation is the primary threat to the patient in the event that a grounded patient electrode loses contact with the patient's body. The patient's body invariably has some electrical contact with ground, either by capacitive coupling or by direct contact with a grounded object. Even with a child, his body is large enough to produce a significant capacitance between his body mass and the grounded operating table. As a result of this relatively low impedance to ground, it is difficult for large voltage differences to exist between the patient's body and ground. Therefore, when RF leakage currents leave the patient's body and go to ground via small, grounded contact points, they do so by direct ohmic connection. In order for electric sparks to jump from the patient's body to ground a voltage difference of over 1000 volts is needed. As a result, a patient electrode related burn is almost always in the desiccation mode.

It is possible that if a small grounded contact were the only electrical connection to ground, then a burn at this location could proceed from desiccation to fulguration after the burn site acquired a high impedance because of the electrosurgical action at that point. However, even in this case, it is clear that the fulguration burn could not have occurred if the desiccation had not taken place first.

Unfortunately, desiccation is usually needed at the site of surgery even though the intention is to cut or fulgurate. That is, in most electrosurgery, desiccation is combined with cutting or fulguration because the surgeon usually starts his cut or fulguration with the electrode in firm contact with the tissue. Since, by definition, the starting mode is desiccation, the desiccation must be complete before the tissue in contact with the electrode will acquire a high enough impedance so that sparking can begin and cutting or fulguration will occur. A typical prior art generator produces over an ampere of desiccation current to necrose and dry the tissue at the active electrode so that the tissue impedance will rise to the requisite amount.

In aforementioned related Application No. 1, a feedback system is described which limits the electrosurgical current to less than 200 ma so that only arcing (only cutting or fulguration) can take place. When used by itself, a system such as this is safer than an ordinary monopolar electrosurgical system and could even be used without a patient electrode with comparative safety. However, as indicated above, a current limited system cannot be used for most surgery because there is no way to get the electrode started. That is, since the current is limited to less than 200 ma and since at least an ampere is needed to desiccate the tissue so that arcing can commence, the current limited, arc only system cannot be used by itself for most surgery. In the above-mentioned related Application No. 1, the necessary tissue desiccation is effected by providing a separate desiccation generator capable of delivering at least 1 ampere of electrical current through the tissue. Thus not only is a capability provided for initiating current limited fulguration or cutting but also the advantages inherent in desiccation vis-a-vis fulguration in certain applications are realized. For example, neural tissue is so fragile that if one attempts to fulgurate a bleeder, the hard surface eschar seals the bleeder but in doing so shrinks and pulls the surface or the tissue so that bleeding may start at the periphery of the eschar. Desiccation does not dry and shrink the tissue as much as fulguration and thus this mode more effectively seals neural bleeders. Hence, the use of the separate desiccation generator is advantageous in this application as well as others. However, it is desirable in some situations to effect necrosis of the tissue to thereby permit the establishment the spark needed for fulguration or cutting without employing a high amperage current to do so and thereby avoid the problems associated with such currents as discussed above.

It is thus an object of this invention to provide a system capable of providing (a) desiccation-type tissue necrosis and (b) cutting and/or fulguration where the "desiccation" is effected by cautery and the cutting and/or fulguration is effected by electrosurgery. Although the term "desiccation" is normally used in connection with electrosurgery, the term, in the following specification and claims, will also be used with respect to the tissue necrosis effected by cautery since, at low temperatures, the latter necrosis appears to be very similar if not identical to that caused by electrosurgical desiccation except that it appears to be more shallow. Since the cautery desiccates the tissue, no large currents pass through the patient to effect this function. Further, since the desiccation is not effected electrosurgically, the electrosurgical generator may be optimized for the high output voltage, high output impedance fulguration and cutting functions. That is, heretofore some electrosurgical generators have operated in modes which tend to be incompatible. Hence, it has been difficult to optimize all modes in a single generator. Aforementioned related Application No. 1 provides one solution to this problem and the subject invention another. That is, by implementing the desiccation mode with cautery, the electrosurgical arcing modes can be optimized without compromising the desiccation function in many applications.

It is a further object of this invention to provide in a current limited, cut only or fulgurate only electrosurgical generator, the capability of initiating the requisite arc without passing a large current through the patient's tissue.

It is a further object of this invention to effect the arc initiating function by employing cautery.

It is a further object of this invention to provide an electrosurgical generator of the above type in combination with a cautery power source where the electrosurgical generator and cautery power source both energize an electrode/heater element.

It is a further object of this invention to provide a combined electrosurgery/cautery system of the above type wherein the cautery is used for (a) tissue coagulation to effect shallow necrosis thereof and/or (b) cutting of the tissue.

It is a further object of this invention to provide a combined electrosurgery/cautery system of the above type wherein the electrosurgical function effects the fulgurate only mode when the cautery function is also employed to effect the cut mode of operation.

It is a further object of this invention to provide a combined electrosurgical/cautery system of the above type having a very small patient electrode or none at all.

It is a further object of this invention to provide different electrosurgical/cautery devices for use in combined systems of the above type.

Other objects and advantages of this invention will be apparent from a reading of the following specification and claims taken with the drawing.

BRIEF DESCRIPTION OF THE DRAWING

FIG. 3 is a circuit diagram of an illustrative, isolated power supply for a cautery source.

FIG. 4 is a circuit diagram of an illustrative arc only, electrosurgical generator.

FIG. 5 is a circuit diagram of an illustrative electrosurgery-cautery system having an alternating current cautery power supply.

FIG. 6 is a diagrammatic drawing of an illustrative transformer containing handpiece in accordance with the invention.

FIG. 7 is a diagrammatic drawing of an illustrative resectoscope in accordance with the invention.

FIG. 8A is a diagrammatic drawing illustrating the manufacture of a high resistance heater element for use in this invention while FIG. 8B is a diagrammatic drawing illustrating the wire of FIG. 8A employed as a high resistance cautery resection loop.

FIG. 9 is a diagrammatic drawing illustrating the manufacture of a high resistance blade in accordance with the invention.

FIG. 10 is a diagrammatic drawing of an illustrative electrosurgery-cautery system having a battery containing handpiece.

DETAILED DESCRIPTION OF THE PREFERRED EMBODIMENTS OF THE INVENTION

Figure 1:
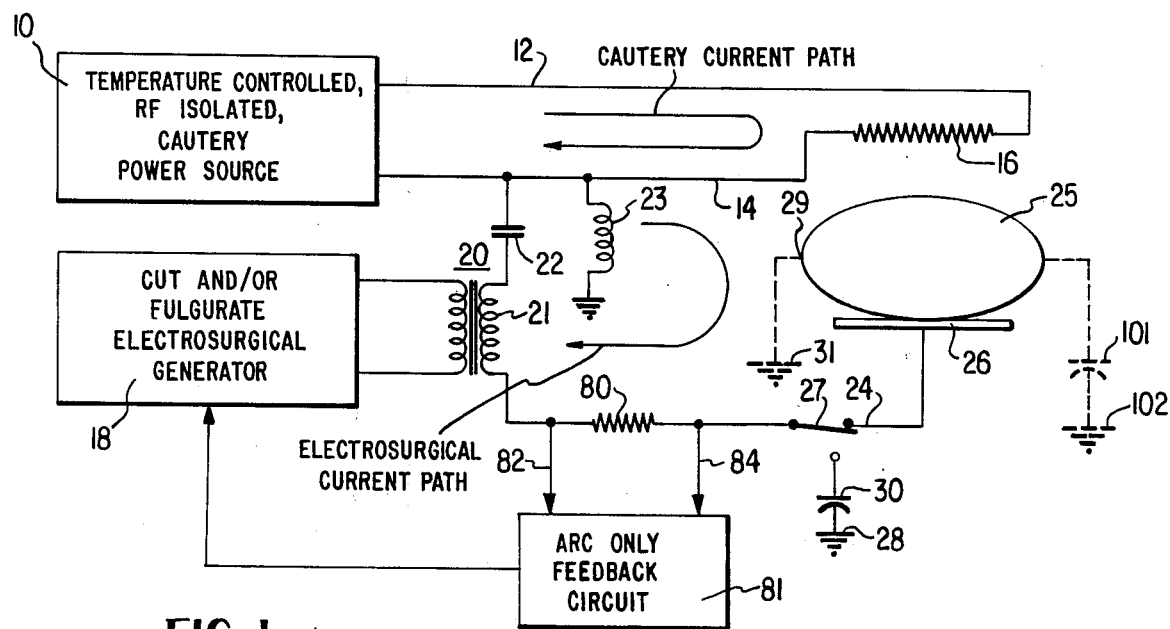
FIG. 1 is a schematic diagram of an illustrative, basic electrosurgery-cautery system in accordance with the invention.

Reference should be made to the drawing where like numerals refer to like elements.

In FIG. 1 there is illustrated a basic electrosurgery/cautery system. A temperature controlled, RF isolated, cautery power source 10 is connected via wires 12 and 14 to a heater/electrode element 16. A cut and/or fulgurate electrosurgical generator 18 is connected via isolation transformer 20 and coupling capacitor 22 to line 14. The low side of the secondary winding 21 is connected via patient lead 24 to patient electrode 26. Lead 24 may be connected to ground 28 by optional capacitor 30 via a single pole, double throw switch 27.

The cautery current path is indicated in FIG. 1 and includes wire 12, heater/electrode element 16 and wire 14. The electrosurgical current path is also indicated and includes coupling capacitor 22, wire 14, element 16, the patient's body 25, patient electrode 26 and patient lead 24.

The cautery system should include the following features: (a) rapid heating and rapid cooling are desired so that the hot electrode does not need a special holster when it is not being used; (b) temperature feedback control is needed so that the electrode tip temperature can be adjusted for performing cautery without tissue sticking; and (c) the electrode heating system needs to be electrically isolated from ground because an electrosurgical electrode must be isolated from ground, insofar as possible.

The temperature control of the cautery element can be done by two basic methods, both of which are known. Thus, a thermocouple or themistor temperature sensing element can monitor the temperature of element 16 and feedback can modify the current through the element to achieve and maintain the desired temperatures. However, the preferred method of temperature measurement is to make element 16 from a material having a large resistive temperature coefficient so that the change of resistance with heating can be used to measure the temperature of the heater and thus control the current which heats the heater. This basic temperature control can be effected by two methods.

Figure 2:
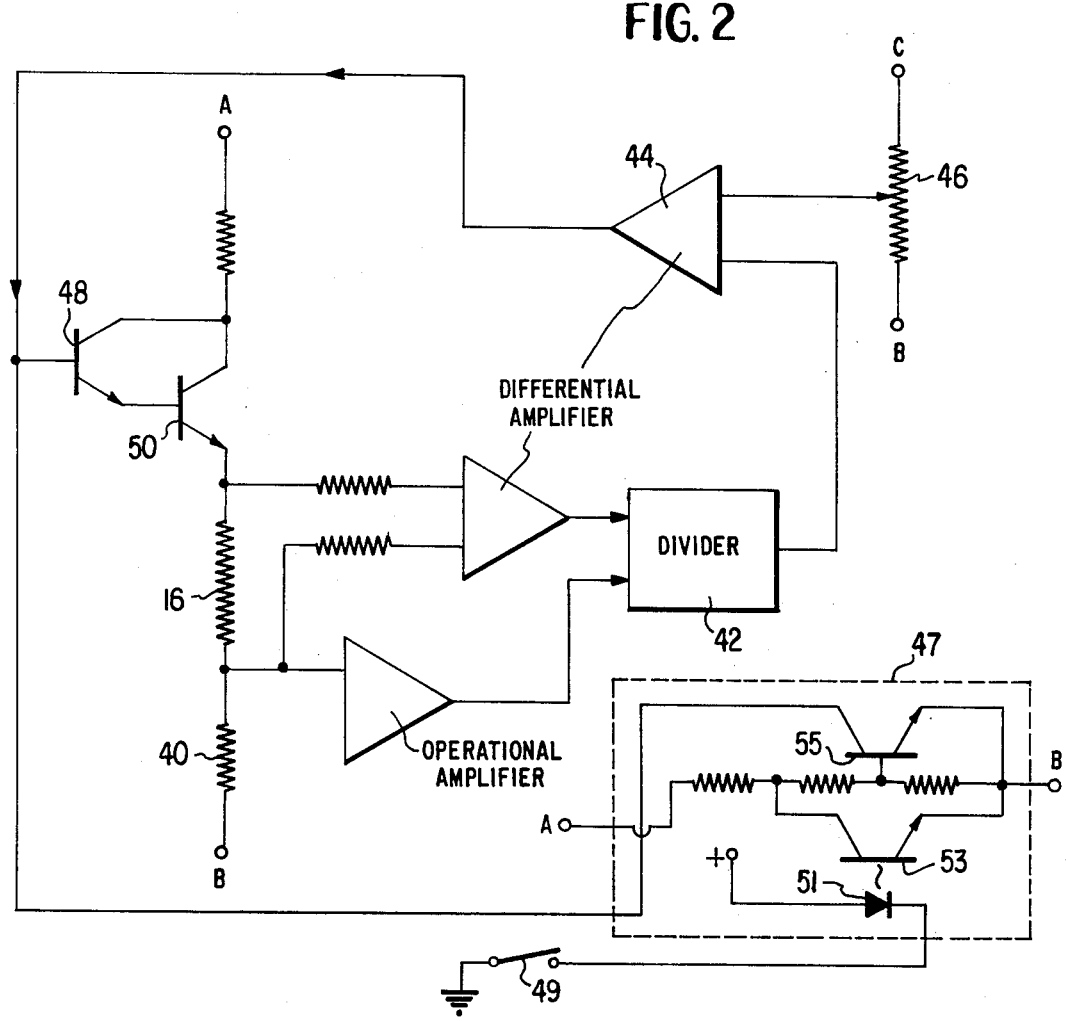
FIG. 2 is a circuit diagram of illustrative circuitry for effecting temperature control of a cautery power source.

In the time sharing method, a small monitor current would be passed through heating element 16 to measure its temperature. For example, the current could be provided by a current source so that it is essentially constant. The voltage drop which is seen across the heater element would be proportional to the resistance of the heater. After a short interval of temperature measurement time, say 10 ms, the large heating current is applied at an amplitude or duration determined by the previous temperature measurement. After the heating interval, say another 10 ms, the system returns to the measurement phase again. The current(s) can be either AC or DC. In the simultaneous method, the heating current and the measurement current are one and the same. Since the current amplitude is not a constant, and the driving voltage is not constant, the value of current must be divided into the voltage to obtain the cautery element resistance, and therefore the temperature. Such a system is illustrated in FIG. 2 which illustrates a typical cautery power source 10 which may be used in the system of FIG. 1. In FIG. 2, a DC current drives the heater element 16. This current also passes through a series current sensing resistor 40, the resistance of which doesn't vary. Therefore, the voltage drop across resistor 40 is an accurate measure of the current passing through the heater element 16. By dividing the voltage drop across the heater 16 by the voltage drop across the current sensing resistor 40, the continuously changing current is cancelled as indicated by equation (1) below. The output of divider 42 is a DC voltage which is directly proportional to the temperature of the heater 16.

$$\frac{\text{heater 16 voltage}}{\text{resistor 40 voltage}} = \frac{IR(T)}{IR'} = \frac{R}{R'}(T) \qquad (1)$$

The resultant DC voltage is used to control the heater current. A differential amplifier 44 compares the temperature dependent voltage with a voltage from a potentiometer 46 to adjust the temperature. The cautery power source is activated by a foot-switch 49 via RF isolated keying circuit 47 which ungrounds the input to the heater current controlling transistors 48 and 50. Keying circuit 47 may comprise a photo-isolator and in particular, a light emitting diode 51 which is actuated when foot switch 49 is closed, a phototransistor 53 which is responsive to LED 51 and NPN transistor 55.

Hence, the circuitry of FIG. 2 utilizes a DC current to energize element 16. AC current sources are also known for effecting this function. Prior art circuitry using DC and/or AC sources is illustrated, for example, by U.S. Pat. Nos. 3,025,706; 3,296,866; 3,406,335; 3,587,318; 3,700,933; 3,789,190; 3,826,263; 3,869,597; and 3,875,503.

From the foregoing it can be seen the cautery portion of the system of FIG. 1 includes electrically heated element 16 incorporated into an electrosurgical electrode. The heat from the element 16 sears the surface of the tissue to produce the impedance change required to initiate arcing. Further, the electric cautery operated by itself is a useful surgical tool which is capable of two distinctly different surgical effects. When operated at relatively low temperatures, 95° to 120° C. (as established by potentiometer 46), it produces a tissue necrosis that may be identical to electrosurgical desiccation except that it is relatively superficial. If the temperature is kept below 120° C., the necrotic tissue remains soft and moist and does not adhere to the electrode. If the cautery probe temperature is kept very high (as again established by potentiometer 46), it can boil surface water and even volatilize tissue. In fact, the cautery wire electrode can cut tissue as efficiently as electrosurgery.

Isolation of the circuitry of FIG. 2 (or any other cautery power source) from ground may be effected by the isolated power supply of FIG. 3. An oscillator generally indicated at 60 generates a driving signal of typically 300 KHz which is applied to a push-pull amplifier indicated at 62 via a driver 61. The oscillator 60, driver 61 and amplifier 62 are chassis ground referenced. The use of a 300 KHz signal is advantageous in that any AC leakage which is inadvertently coupled to the element 16 is at too high a frequency to stimulate muscles or nerves and/or to interfere with ECG patient monitors. The output of amplifier 62 is coupled via an isolation transformer 64 to a diode bridge 66 where it is full wave rectified and then filtered by a filter circuit indicated at 68. A reference voltage C is regulated by zener diode 69. The output terminals A, B and C provide isolated DC voltages to the terminals A, B and C shown in FIG. 2. Thus, the FIG. 2 circuitry is isolated from ground.

A cut only and/or fulgurate only generator which may be used as generator 18 has been described in the aforementioned related Application No. 1. Such a generator is also shown in FIG. 4. In order to limit the current passing through the patient during the fulguration or cut modes of operation and thereby prevent desiccation during these arcing (or sparking) modes, an arc only feedback circuit generally indicated at 81 in FIG. 4 may be employed in the following manner. The current in patient lead 24 (FIG. 3) is sensed by a small resistor 80 serially inserted in patient lead 24. The value of this resistor is typically approximately 0.1 ohms. Leads 82 and 84 connected across resistor 80 are connected to a voltage transformer 86 (FIG. 4) which isolates the current feedback signal from the RF output. Thus, a voltage signal proportional to the current is transferred to ground without compromising the RF isolation of the output circuit. This small RF signal is applied to a bridge rectifier 88, the output of the rectifier being smoothed by filter 90. The rectified voltage is then applied to operational amplifier 98. Switch 118 which may be on the console panel determines whether the arc only mode is selected. Assuming the switch 118 is open as shown in FIG. 4 so that an arcing mode has been selected, the voltage fed back from filter 90 is applied to the inverting input of operational amplifier 98 which in turn is connected to an operational amplifier 100. Applied to the non-inverting input of operational amplifier 100 over line 103 is the output from a potentiometer 108 where potentiometer 108 is connected between reference voltage source 114 and ground. The purpose of potentiometer 108 is to control the level of the cut and/or fulgurate waveform(s) applied to the patient. The purpose of the feedback voltage at the output of amplifier 98 is to decrease the control voltages developed by potentiometer 108 in accordance with the sensed current passing through the patient. The sensitivity of operational amplifier 100 is regulated by potentiometer 116. The output of operational amplifier 100 is applied to driver 70 and output stage 72. Hence, the output of amplifier 100 is employed to regulate the output power of source 18. In particular, negative current feedback is employed to limit the current to typically no more than 200 ma in the arcing modes of operation and to thereby prevent desiccation in these modes of operation where the response time of the feedback circuit should be at least less than 10 milliseconds (ms) and preferably less than 1 ms to avoid significant desiccation immediately after the element 16 contacts the patient's tissue. Alternatively, positive voltage feedback could also be employed to effect the desired current limiting although such a feedback arrangement is not preferred because of the tendency for the system to oscillate.

Driver 70 and output stage 72 may be as described in U.S. Pat. No. 3,963,030 granted to D. Newton which is hereby incorporated herein by reference. Thus, the feedback circuitry of FIG. 4 would be such that the width of the inductor charging current pulses from the generator disclosed in U.S. Pat. No. 3,963,030 would be controlled in accordance with the amount of negative current feedback from amplifier 98 to thereby maintain the average patient current below a predetermined minimum such as 200 ma. In particular, potentiometer 88 of FIG. 4 of U.S. Pat. No. 3,963,030 corresponds to potentiometer 108 of the present invention. The output of potentiometer 88 would be connected to the non-inverting input of operational amplifier 100 of the present invention while the output of operational amplifier 100 would be connected to the anode of diode 91 of FIG. 4 of U.S. Pat. No. 3,963,030 whereby the desired pulse width control would be effected in response to the feedback current from operational amplifier 98 of the present invention.

Alternatively, the amplitude of the bursts can be controlled directly. Thus, in U.S. Pat. No. 3,699,967 granted to R. Anderson (which is hereby incorporated herein by reference), the output of operational amplifier 100 of the present invention may be used to change the position of the tap of potentiometer R30 in FIG. 4 of U.S. Pat. No. 3,699,967 via a servomechansim (not shown) whereby the amplitude of the fulgurate bursts would be controlled in accordance with the amount of feedback from operational amplifier 98 of the present invention.

Alternatively, driver 70 and output stage 72 may correspond to the cut current source of U.S. Pat. No. 3,699,967 corresponding to the astable multivibrator of FIG. 4 thereof. In order to regulate the output of the multivibrator in acordance with the feedback output from operational amplifier 98 of the present invention, the position of the tap of potentiometer R31 of U.S. Pat. No. 3,699,967 may be changed via a servomechanism by the output of operational amplifier 100 of the present invention.

It is also within the scope of the present invention to utilize the common cut/fulgurate source disclosed in above U.S. Pat. No. 3,699.967 where transformer T2 of FIG. 3 thereof would take the place of transformer 20 of FIG. 1 of the present invention.

In accordance with a further possible modification, arc only feedback circuit 81 may be eliminated whereby the output impedance of source 18 can be made large by providing a relatively large number of turns on secondary winding 21 to thereby effect the arc only mode of operation. However, it is preferable to employ the feedback circuit 81 to effect this mode.

In accordance with a further aspect of this invention, the size of patient electrode 26 may be quite small (less than 60 sq. cm. and typically as small as 2 sq. cm.) and in many applications it may be eliminated altogether. The patient's body is quite often at or very near ground potential either because of a direct connection to ground or because of the large capacitance 101 (see FIG. 1) of the patient's body with respect to ground. Hence, assuming no patient plate is employed (whereby switch 27 is actuated to connect resistor 80 to ground 28 via capacitor 30), an electrosurgical current path is nevertheless present from element 16 through the patient's body 25 and capacitance 101 (assuming there is no direct connection to ground) to ground 102. The current returns to the low side of the secondary 21 via ground 28 and resistor 80. The current that flows in this path is limited to the value established by generator 18 and arc only feedback circuit 81. Hence, there is little, if any, danger of a desiccation burn occurring at an inadvertent grounding point on the patient even if the contact area of the inadvertent ground is very small and even if there is no patient electrode 26. Such an inadvertent grounding point is indicated at 29, ground being indicated at 31. Further, appropriate steps may be taken to limit the current from generator 18 to a safe value corresponding to the smallest anticipated grounding point.

Switch 27 is positioned as shown in FIG. 1 when a return electrode such as return electrode 26 is employed. In this position of the switch, the return lead 24 is isolated from ground. Thus, if the patient loses contact with return electrode 26, there is little, if any, danger to the patient if he is in contact with a small inadvertent ground such as grounded contact point 29. That is, not only is the current limited because the current may be limited by the arc only feedback circuit 81 but also it is limited because of the high impedance between ground and return lead 24.

There is some tendency for the arc only feedback circuit 81 to be effected by leakage current from active lead 12,14 to ground inasmuch as this current returns to the low side of transformer 20. Some of the current passes through resistor 80 where, ideally resistor 80 senses only the current passing through the patient. The effect of the active lead leakage current is lessened by the isolation of lead 24 when switch 27 is in the position shown in FIG. 1. When the switch connects resistor 80 to ground 28, the effect of the leakage current tends to increase. Regardless of the position of switch 27, the effect of the leakage current can be further lessened by connecting an inductor 23 between active lead 14 and ground to thereby at least partially cancel the active lead leakage current. The use of such as inductor is described in U.S. Pat. No. 3,946,738 granted to D. Newton, see FIG. 2 thereof, this patent being incorporated herein by reference.

It is desirable that the wires 12 and 14 leading from the generators to the handpiece 34 be light weight and suitable for mass production and possibly even part of a disposable system. The magnitude of the heating current for the cautery element depends on the amount of resistance in the heating element 16. Referring to FIG. 5, there is illustrated a particular embodiment where the heating element 16 may comprise a short piece of resistance wire, the resistance of which is quite low, typically one or two ohms at most and typically no more than 10 ohms. In the case of a one or two ohm resistance, a large current of 5 to 10 amperes is needed to produce, say 25 to 100 watts of of power. To avoid large voltage drops across wires 12 and 14 (these wires preferably being fine gauge, for example, 22 gauge), a current step-up transformer 36 is disposed in handpiece 34 which changes the current ratio before it goes through heating element 16. Power source 10 provides AC heating and measurement currents due to the presence of current transformer 36 in the handpiece. Because of the danger of low frequency leakage currents to the patient and because of the large iron transformer cores required for low AC frequencies, the AC frequency should be as high as possible without introducing excessive reactive impedances into the system that would tend to distort the heating element resistance measurements. The optimum frequency is around 120 KHz. Since all the currents are high frequency AC, including the electrosurgical currents from generator 18, the isolation of the acitve electrode/heating element 16 from ground is easily accomplished with transformers 20 and 32. Capacitor 38 acts as a bypass capacitor for the electrosurgical current.

In FIG. 6 there is shown an illustrative handpiece 34 for use with the FIG. 5 system where a "blade" electrode 16 is formed from a hairpin shaped low resistance wire and transformer 36 is disposed within the handpiece.

The low resistance heater element 16 of FIG. 5 has several advantages:

(1) It is easy to manufacture. Further, certain configurations of the element would be very similar to existing wire electrodes used in electrosurgery. For example, the resectoscope used for transurethral resections uses a loop of wire as n electrode. If this loop of wire were also a cautery element, the resulting instrument would be very similar to resectoscopes used today and would operate in the same manner, except that the high desiccation currents, urethral strictures and burns due to faulty patient electrodes would be extremely unlikely. Reference should be made to FIG. 7 which shows an illustrative resectoscope employing a cautery element resection loop 16 in accordance with an aspect of this invention where the resectoscope conventionally includes optical telescope 120, eyepiece 122 and finger ring 124 for moving loop 16 back and forth. Loop 16 is connected to transformer 36 as shown in FIG. 7.

(2) In polypectomy, the procedure involves the removal of polyps from the gastrointestinal tract by means of a wire snare looped around the stalk of the polyp. Such a snare wire may correspond to a cautery wire 16 of FIG. 7 and would eliminate the complications of the "contralateral burn" and excessive desiccation which sometimes causes a patient to go to surgery because of a perforated bowel.

(3) The simplicity of the wire electrode 16 itself lends itself well to mass production and disposability.

The disadvantages of the wire cautery element are:
(1) the low resistance requires large currents for heating and either AC transformer 36 or large connecting cables 12 and 14 must be used, both of which tend to be expensive and not suitable for use in disposable systems; and (2) the use of two transformers 32 and 36 in the circuit between generator 10 and heating element 16 and a relatively high frequency means that the temperature measurement will have a number of sources of error and will be difficult to calibrate.

Use of a high resistance heater element as element 16 of FIG. 1 avoids the foregoing problems but tends to introduce other ones. Advantages of the high resistance heater element are that (1) small heating currents can be used, either as AC or DC; (2) good temperature measurement accuracy is readily obtained; and (3) no transformers are required in the handpiece because the heating current is low. Although somewhat difficult at this time, it is possible that some forms of high resistance electrodes could be mass produced, lending the whole active assembly (wire 12, 14, handpiece 34, and electrode/heater 16) to mass production and a disposable product.

Referring to FIG. 8A, a high resistance electrode element 16 can be made by winding a very fine, high resistance wire 126 around a non-conducting bundle of heat resistant fibers 128 such as glass. This composite wire may then be bent into loop electrodes for polypectomy or transurethral resections as shown in FIG. 8B.

Referring to FIG. 9, it is also possible to build blade electrodes by printing or depositing a film 130 of low resistance carbon or metal (such as a nickel alloy) on a ceramic base 132. The resistance can be fairly high if the film is printed in a narrow, zig-zag line as shown in FIG. 9. The entire blade should then be covered with a thin film 134 of very high resistance, conductive material such as carbon which has been processed to give it a high resistivity to protect the metal film and give the advantages of the carbon coated electrode blades disclosed in U.S. patent application Ser. No. 667,849 filed Mar. 17, 1976 by Charles F. Morrison and assigned to the assignee of the present invention where the foregoing patent application is hereby incorporated herein be reference. The carbon coating must be very resistive so that it won't substantially short out the lines of metal film.

Reference should be made to FIG. 10 for a further embodiment of the invention wherein a battery 140 is incorporated in handpiece 34 to provide the heating current for element 16, the element 16 being in series circuit with heavy conductor 142 which extends from the terminals of battery 140 whereby the heating effect is effectively localized in element 16. Switch 144 incorporated on handpiece 34 permits energization of element 16. Battery 140 is perferably of the rechargeable type such as a lead-acid rechargeable battery. The battery may be recharged from a low voltage DC supply 146 which is connected to the battery by lines 12 and 14 where line 14 is connected to generator 18 as shown in FIG. 1. Circuitry (not shown) may also be connected to battery 140 over lines 12 and 14 to monitor DC voltage and/or current and thus provide means for measuring and possibly controlling the temperature of element 16. It can thus be seen that in the embodiment of FIG. 10, battery 140 serves the function of the cautery power source 10 of FIG. 1 and permits the use of fine gauge wire for wires 12 and 14 while at the same time permitting a low resistance heating element.

What is claimed is:

1. A combined electrosurgery and cautery system for use with a patient, said system comprising
a combined heater and electrode element;
cautery power supply means for applying a first electrical current through said combined heater and electrode element to heat said element, said cautery power supply means including means for passing said first current through said element back to the cautery power supply means without passing through said patient so that tissue of said patient is necrosed by said first current in response to the element being positioned adjacent the tissue;

electrosurgical generator means for applying a second electrical current to said combined heater and electrode element, said electrosurgical generator means including means for passing said second current through said patient back to the electrosurgical generator means where said electrosurgical generator means produces a voltage on said element, the magnitude of which is sufficiently high to permit arcing from the element to the patient after said tissue has been necrosed by said first current.

2. A system as in claim 1 including current limiting means for limiting said second electrical current through said patient to an arcing only value at which desiccation of the patient's tissue is not likely.

3. A system as in claim 2 where said arcing only value is not more than about 200 ma.

4. A system as in claim 2 where said electrosurgical generator means includes power adjusting means for adjusting the output power delivered to said combined heater and electrode element and where said current limiting means includes feedback means for providing a feedback signal from said element, said power adjusting means being responsive to said feedback signal to thereby limit said second current to said arcing only value.

5. A system as in claim 2 including a first isolation transformer, the primary winding of which is connected to said electrosurgical generator meanns and the secondary winding of which is connected to said combined heater and electrode element and where the output impedance of said transformer is sufficiently high to limit said second current to said arcing only value.

6. A system as in claim 1 including a handpiece adapted for manual manipulation, said combined heater and electrode element being mounted on said handpiece and a current step-up transformer disposed within said handpiece, the secondary winding of said transformer being connected across said element and first and second wires connected from said cautery power supply means to the respective ends of the primary winding of said transformer whereby said wires may be of a fine gauge due to the current step-up effected by the transformer.

7. A system as in claim 6 where said cautery power supply means is an alternating current source, the frequency of which is high enough to avoid neuromuscular stimulation.

8. A system as in claim 7 where the frequency of said alternating current is about 120 KHz.

9. A system as in claim 8 including an isolating transformer, the primary winding of which is connected to said cautery power supply means and the secondary of which is respectively connected to said first and second wires.

10. A system as in claim 6 where said electrosurgical generator means is connected to one of said first and second wires.

11. A system as in claim 1 including means for isolating said cautery power supply means from ground.

12. A system as in claim 1 where said cautery power supply means is an alternating current source.

13. A system as in claim 1 wherre said combined heater and electrode element comprises a resistance wire wound about an electrically insulative core.

14. A system as in claim 13 where said core comprises glass fibers.

15. A system as in claim 1 where said combined heater and electrode element comprises a substrate of electrically insulating material, an electrically conductive wire deposited thereon, said wire being connected to said cautery power supply means and said electrosurgical generator means and a high resistivity, conductive covering disposed over said electrically conductive wire.

16. A system as in claim 15 where said substrate comprises a ceramic material, said wire comprises a nickel alloy and said cover comprises a carbon film.

17. A system as in claim 1 where said combined heater and electrode element has a loop configuration.

18. A system as in claim 17 including means for moving the loop in a predetermined direction whereby the loop may be encircled about a growth or the like on the patient to thereby effect electrosurgical removal of the growth.

19. A system as in claim 17 where said loop configuration is an elongated hairpin configuration.

20. A system as in claim 1 including means for regulating the amount of said first current passing through said combined heater and electrode element to thereby maintain the temperature of said element at a predetermined value.

21. A system as in claim 20 including means for establishing the predetermined value of the temperature of said combined heater and electrode element.

22. A system as in claim 21 where said temperature establishing means includes means for setting the temperature of said element to a value which will cause desiccation of the patient's tissue.

23. A system as in claim 22 where said temperature establishing means includes means for setting the temperature of said element to a value which will cause cutting of the patient's tissue.

24. A system as in claim 1 where said cautery power supply means is a direct current source.

25. A system as in claim 24 including a handpiece upon which is disposed said combined heater and electrode element and where said direct current source comprises a battery disposed within said handpiece.

26. A system as in claim 25 including means for recharging said battery.

27. A system as in claim 1 including a return electrode adapted for contact with said patient, said return electrode being connected to said electrosurgical generator means to thereby provide a return path for said second current to said electrosurgical generator means.

28. A system as in claim 27 where the surface area of said return electrode adapted for contact with said patient is no more than 60 square centimeters.

29. A system as in claim 28 where said surface area is no more than 10 square centimeters.

30. A system as in claim 27 including switching means having a first position in which said return electrode is connected to said electrosurgical generator means and a second position in which said electrosurgical generator means is disconnected from said return electrode and connected to ground so that, when no return electrode is employed, a return path for said second current is provided through said patient to said ground and then from said ground back to the electrosurgical generator means.

31. A system as in claim 1 including means for providing the intended return path for said second current through said patient to ground and then from said ground back to the electrosurgical generator means whereby a large area return electrode does not have to be applied to said patient to provide a return path for said second current.

32. A system as in claim 1 where said combined heater and electrode element comprises a cautery heater and an electrosurgical electrode.

33. A system as in claim 32 where cautery heater and said electrosurgical electrode are one and the same element.

34. An electrosurgical method comprising
placing a combined heater and electrode element adjacent tissue to a patient to be treated;
passing a first current through said combined heater and electrode element to effect necrosis of said tissue where said first current is passed through said element without passing through said tissue; and
passing a second current through said combined heater and electrode element and through said patient so that an arc is established between said element and said patient after the tissue is necrosed by said first current.

35. A method as in claim 34 where the magnitude of said second current is less than that which is needed to initiate said arc.

36. A method as in claim 35 where said magnitude of the second current is not more than about 200 ma.

37. A method as in claim 34 where said second current comprises a sine wave suitable for cutting said tissue.

38. A method as in claim 34 where said second current comprises bursts of high frequency electrical energy suitable for fulguration of said tissue.

39. A method as in claim 34 where said second current passes directly from said patient without passing through a return electrode.

* * * * *